(12) United States Patent
Liu et al.

(10) Patent No.: US 10,799,201 B2
(45) Date of Patent: Oct. 13, 2020

(54) C-ARM IMAGING SYSTEM HAVING COAXIAL INDEPENDENT ROTATION OF MONITORS

(71) Applicant: General Electric Company, Schenectady, NY (US)

(72) Inventors: Mingtao Liu, Beijing (CN); Cong Peng, Beijing (CN); Yu Zhang, Beijing (CN); Jundong Li, Beijing (CN)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 129 days.

(21) Appl. No.: 15/894,466

(22) Filed: Feb. 12, 2018

(65) Prior Publication Data

US 2019/0246998 A1    Aug. 15, 2019

(51) Int. Cl.
*A61B 6/00* (2006.01)

(52) U.S. Cl.
CPC ............ *A61B 6/462* (2013.01); *A61B 6/4441* (2013.01); *A61B 6/464* (2013.01)

(58) Field of Classification Search
CPC ........ A61B 6/462; A61B 6/4441; A61B 6/464
See application file for complete search history.

(56) References Cited

U.S. PATENT DOCUMENTS

| | | | | |
|---|---|---|---|---|
| 5,434,903 A * | 7/1995 | Hoornaert | ............ | A61B 6/4441 378/101 |
| 6,256,374 B1 * | 7/2001 | Tomasetti | ............ | A61B 6/4441 378/198 |
| 6,899,442 B2 * | 5/2005 | Howell | ............ | E04B 9/006 248/278.1 |
| 7,644,898 B2 * | 1/2010 | White | ............ | A61B 90/50 211/26 |
| 8,424,833 B2 * | 4/2013 | Muller | ............ | F16M 11/08 248/324 |
| 2003/0233040 A1 * | 12/2003 | Sakaniwa | ............ | A61B 6/4464 600/407 |
| 2010/0054543 A1 * | 3/2010 | Pachys | ............ | G01N 23/046 382/110 |
| 2010/0239073 A1 * | 9/2010 | Eaves | ............ | A61B 6/4233 378/198 |
| 2010/0296626 A1 * | 11/2010 | Hibino | ............ | A61B 6/04 378/44 |
| 2012/0016222 A1 * | 1/2012 | Bouvier | ............ | A61B 6/102 600/407 |
| 2013/0044859 A1 * | 2/2013 | Yabugami | ............ | G01N 23/04 378/62 |
| 2014/0233702 A1 * | 8/2014 | Suzuki | ............ | A61B 6/42 378/62 |
| 2018/0214112 A1 * | 8/2018 | Graziani | ............ | A61B 6/547 |
| 2019/0150865 A1 * | 5/2019 | Johnson | ............ | A61B 6/4405 |

OTHER PUBLICATIONS

Ziehm Solo, "Superb imaging meets versatile design" https://www.ziehm.com/uploads/media/US_Ziehm_Solo_brochure_2016-08-20_01.

* cited by examiner

*Primary Examiner* — Marcus H Taningco
(74) *Attorney, Agent, or Firm* — Fletcher Yoder, P.C.

(57) ABSTRACT

A C-arm X-ray imaging system is provided. The C-arm X-ray imaging system includes a base, an extension arm, a first monitor coupled to the base via a first end of the extension arm, a support, and a second monitor coupled to the base via the support. The first end of the extension arm and the support are vertically aligned and configured to rotate about a common rotational axis to enable independent rotation of the first and second monitors.

15 Claims, 4 Drawing Sheets

C-ARM IMAGING SYSTEM HAVING COAXIAL INDEPENDENT ROTATION OF MONITORS

BACKGROUND

The subject matter disclosed herein relates to X-ray imaging systems having C-arms and, more particularly, to X-ray imaging systems having different monitors coupled to the X-ray imaging system that rotate relative to the X-ray imaging system.

Medical diagnostic imaging systems generate images of an object, such as a patient, for example, through exposure to an energy source, such as X-rays passing through a patient, for example. The generated images may be used for many purposes. Often, when a practitioner takes X-rays of a patient, it is desirable to take several X-rays of one or more portions of the patient's body from a number of different positions and angles, and preferably without needing to frequently reposition the patient. To meet this need, C-arm X-ray diagnostic equipment has been developed. The term C-arm generally refers to an X-ray imaging device having a rigid and/or articulating structural member having an X-ray source and an image detector assembly that are each located at an opposing end of the structural member so that the X-ray source and the image detector face each other. The structural member is typically "C" shaped and so is referred to as a C-arm. In this manner, X-rays emitted from the X-ray source can impinge on the image detector and provide an X-ray image of the object or objects that are placed between the X-ray source and the image detector.

In many cases, C-arms are connected to one end of a movable arm. In such cases, the C-arm can often be raised and lowered, be moved from side to side, and/or be rotated about one or more axes of rotation. Accordingly, such C-arms can be moved and reoriented to allow X-ray images to be taken from several different positions and angles and different portions of a patient, without requiring the patient to be frequently repositioned. These X-ray devices having a C-arm may also include multiple monitors coupled to the X-ray device to enable different medical personnel (e.g., doctor, technician, etc.) to perform their respective tasks during an imaging procedure. Typically, the medical personnel have different tasks and are located in different positions relative to the X-ray device. However, rotation of one of the monitors may result in movement of the other monitor and interference with the other person's task.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible forms of the subject matter. Indeed, the subject matter may encompass a variety of forms that may be similar to or different from the embodiments set forth below.

In accordance with a first embodiment, an X-ray imaging system is provided. The X-ray imaging system includes an X-ray radiation source, an X-ray detector, and a C-arm having the X-ray radiation source disposed on a first end and the X-ray detector disposed on a second end opposite the first end. The X-ray imaging system also includes a base coupled to the C-arm, a first monitor coupled to the base, and a second monitor coupled to the base. The first monitor and the second monitor are configured to rotate independent of each other about a common rotational axis.

In accordance with a second embodiment, a C-arm X-ray imaging system is provided. The C-arm X-ray imaging system includes a base, an extension arm, a first monitor coupled to the base via a first end of the extension arm, a support, and a second monitor coupled to the base via the support. The first end of the extension arm and the support are vertically aligned and configured to rotate about a common rotational axis to enable independent rotation of the first and second monitors.

In accordance with a third embodiment, a C-arm X-ray imaging system is provided. The C-arm X-ray imaging system includes a base, a first monitor coupled to the base, and a computing device coupled to the base. The computing device includes a second monitor and the computing device is configured to control operation of the C-arm X-ray imaging system. The first monitor and the second monitor are configured to rotate independent of each other about a coaxial axis.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

The following embodiments describe an X-ray imaging system (e.g., compact mobile X-ray imaging system) having a C-arm that includes multiple monitors that rotate in an independent coaxial manner. For example, a first monitor may be coupled to an extension arm coupled to a portion (e.g., arm base) of the X-ray imaging system and a second monitor (e.g., reference monitor or tablet) may be coupled to a support (e.g., tablet support) coupled to the same portion (e.g., arm base). Both the first monitor (via the extension arm) and the second monitor (via the support) may rotate in a coaxial manner about a common axis independent of each other. Coaxial independent movement enables each monitor to be moved within a compact space without moving the other monitor. This enables the medical personnel (e.g., doctor, technician, etc.) to move their respective monitor and to perform their respective tasks without impacting others.

Figure 1:
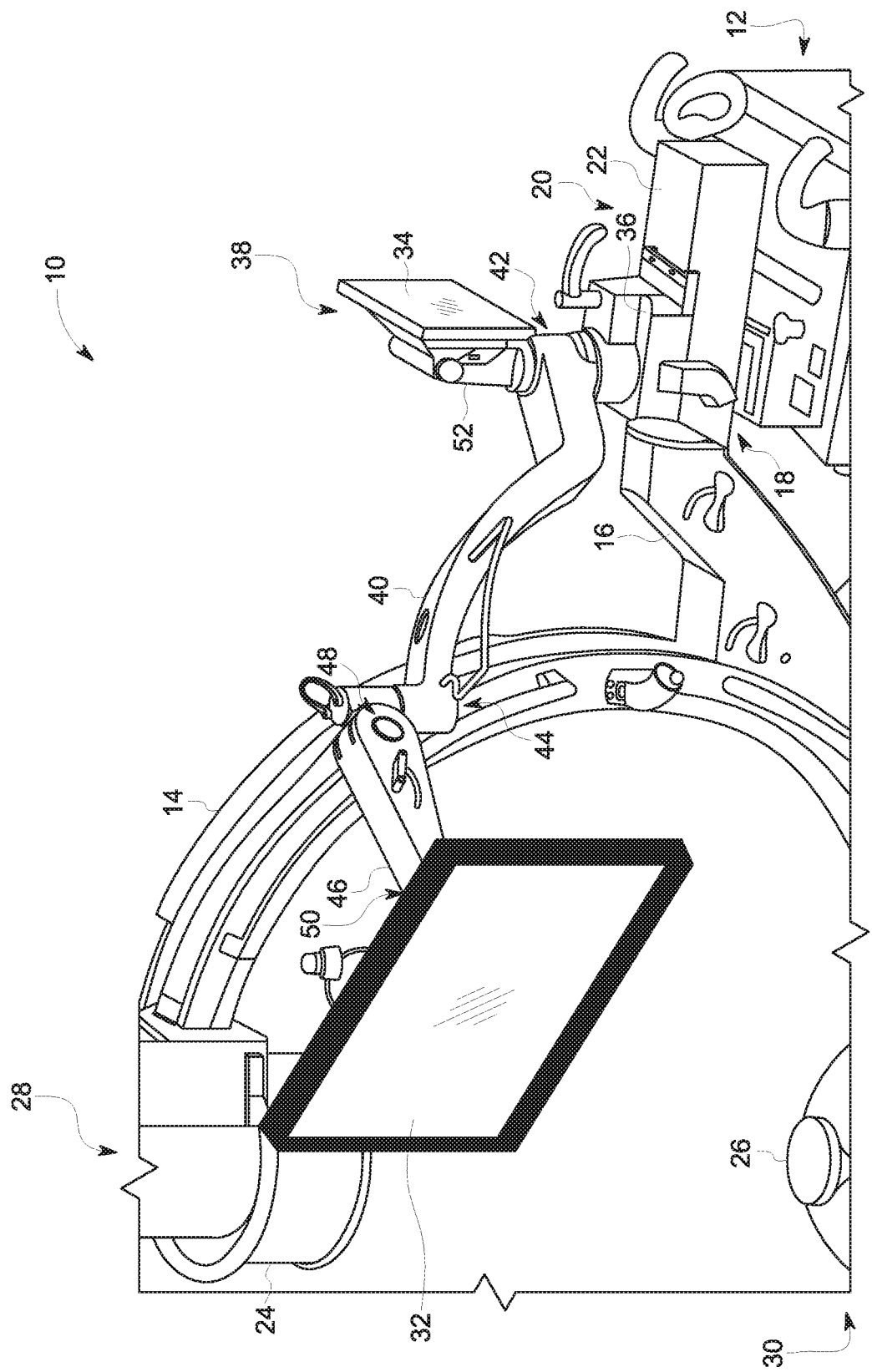
FIG. 1 is a perspective view of an embodiment of a portion of an X-ray imaging system (e.g., a mobile C-arm imaging system) having multiple monitors that rotate in a coaxial and independent manner.

FIG. 1 is a perspective view of an embodiment of an X-ray imaging system 10 (e.g., a mobile C-arm imaging system) having multiple monitors that rotate in a coaxial and independent manner. Although a mobile imaging system is illustrated, the embodiments described below may be utilized with any X-ray imaging system having a C-arm (e.g., a fixed imaging system). The X-ray imaging system 10 may utilize multiple imaging modalities (e.g., fluoroscopy, computed tomography, tomosynthesis, radiographic, magnetic resonance imaging, etc.) to acquire two-dimensional 2D and/or 3D image data. The X-ray imaging system 10 may be utilized for both diagnostic and interventional imaging. In addition, the X-ray imaging system 10 may be utilized for general purposes (e.g., general radiology, orthopedics, etc.) and special purposes (e.g., image guided surgery).

A principal function of the mobile X-ray system is to generate X-rays for diagnostic and interventional imaging. The X-ray system includes a support structure or base 12, a C-arm 14, and an L-arm 16. The base 12 provides support for the C-arm 14 and holds the C-arm 14 in a suspended position. The lower portion of the base 12 includes wheels or casters utilized to provide mobility to the system 10. The base 12 includes a vertical lift column 18 that permits the C-arm 14 and L-arm 16 to move vertically in relation to base 12. Vertical lift column 18 terminates in an upper housing 20 of the base 12, wherein a horizontal extension arm 22 (e.g., cross arm) passes through upper housing 20 and permits arm 16 (as well as the C-arm 14) to move perpendicularly in relation to vertical lift column 18 by movement (e.g., horizontal movement) of the horizontal extension arm 22 in relation to upper housing 20.

An image receptor 24 (e.g., X-ray detector) and an X-ray source 26 are coupled to opposing ends 28, 30 of the C-arm 14 to form an image chain. The C-arm 14 allows the image receptor 24 and the X-ray source 26 to be mounted and positioned about an object to be imaged, such as a patient. The C-arm 14 may be a circular C-shaped or an arc-shaped member, for example. The C-arm 14 enables selective positioning of the image receptor 24 and the X-ray source 26 with respect to the width and length of the patient or other object located within the interior free space of the C-arm 14.

The image receptor 24 may be an image intensifier or other energy receptor for using in diagnostic imaging, for example. The image receptor 24 and the X-ray source 26 are used to generate a diagnostic image representative of the object being imaged.

As depicted, the imaging system 10 includes a first monitor 32 and a second monitor 34 (e.g., reference monitor) coupled to portion 36 (e.g., arm base) of the base 12 that is coupled to the horizontal extension arm 22. The second monitor 34 may be part of a computing device 38 (e.g., tablet computer, computer, etc.). The computing device 38 includes memory circuitry that stores instructions or code and processing circuitry that executes the instructions stored in the memory circuitry. The computing device 38 may be utilized to control operations of the X-ray imaging system 10 (e.g., acquisition of image data, movement of imaging system 10, movement of the C-arm 14, movement of the monitors 32, 34, etc.). The first monitor 32 may be utilized by a doctor and the second monitor 34 may be utilized by a technician during an imaging operation.

The first monitor 32 is coupled to the base portion 36 via an extension arm 40. The extension arm 40 includes ends 42, 44. End 42 is coupled to the base portion 36 and end 44 is coupled to the first monitor 32. Specifically, end 44 is coupled to the first monitor 32 via arm 46 (e.g., spring arm). The spring arm 46 includes ends 48, 50. End 48 is coupled to end 44 of the extension arm 40 and end 50 is coupled to the first monitor 32. The spring arm 46 enables rotation (e.g., in a circumferential direction) of the first monitor 32 relative to the extension arm 40 about a rotational axis where the ends 44, 48 are coupled. The second monitor 34 is coupled to the base portion 36 via a support 52 (e.g., tablet support).

The end 42 of the extension arm 40 is vertically aligned with the support 52 about a common rotational axis or coaxial axis 54 (see FIGS. 2 and 3) with the support 52 located above the end 42. As described in greater detail below, the coupling of the first monitor 32 (via the extension arm 40) and the second monitor 34 (via the support 52) to the base portion 36 enables independent rotation of the first and second monitors 32, 34 about the coaxial axis 54. This enables the first monitor 32 or the second monitor 34 to be moved (e.g., circumferentially) without it affecting the other monitor 32, 34. Thus, the medical personnel (e.g., doctor, technician, etc.) may perform their respective tasks without interference (e.g. due to unwanted movement of their respective monitor) in a tight space on a compact mobile C-arm imaging system.

Figure 2:
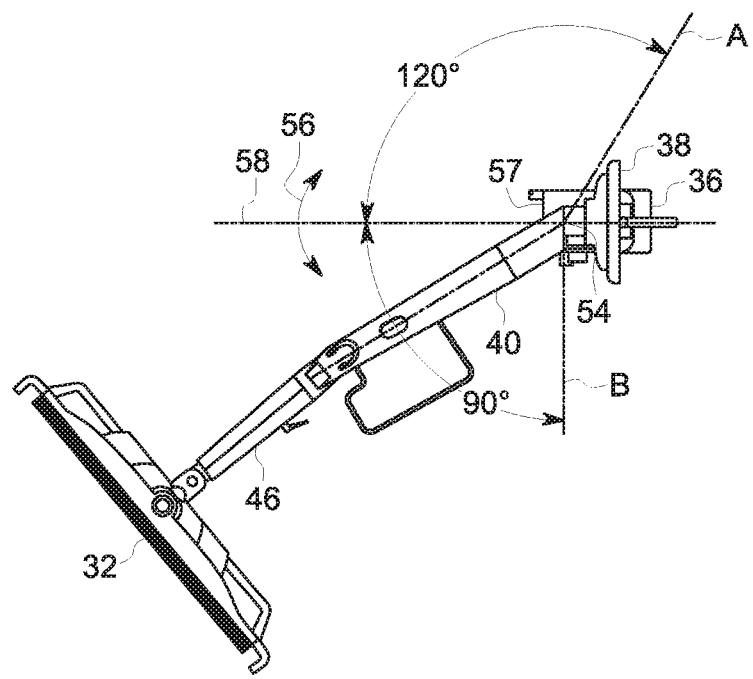
FIG. 2 is a top view of an embodiment of an extension arm having a first monitor and a support for the second monitor coupled to a portion (e.g., arm base) of the X-ray imaging system of FIG. 1 illustrating the rotational movement of the extension arm.

As depicted in FIG. 2, rotation of the extension arm 40 in a circumferential direction 56 about the coaxial axis 54 enables the first monitor 32 to be rotated up to approximately 210 degrees about the axis 54. In particular, the first monitor 32 may be rotated (e.g., on a side 57 of the base portion 36 nearest the C-arm 14) approximately 120 degrees between a longitudinal axis 58 of the base portion 36 (or cross arm 22) and point A (located to the right of the axis 58 relative to the side 57). The first monitor 32 may also be rotated (e.g., on the side 57) approximately 90 degrees (in the opposite direction) between the longitudinal axis 58 and point B (located to the left of the axis 58 relative to the side 57). Point B is orthogonal to the axis 58.

Figure 3:
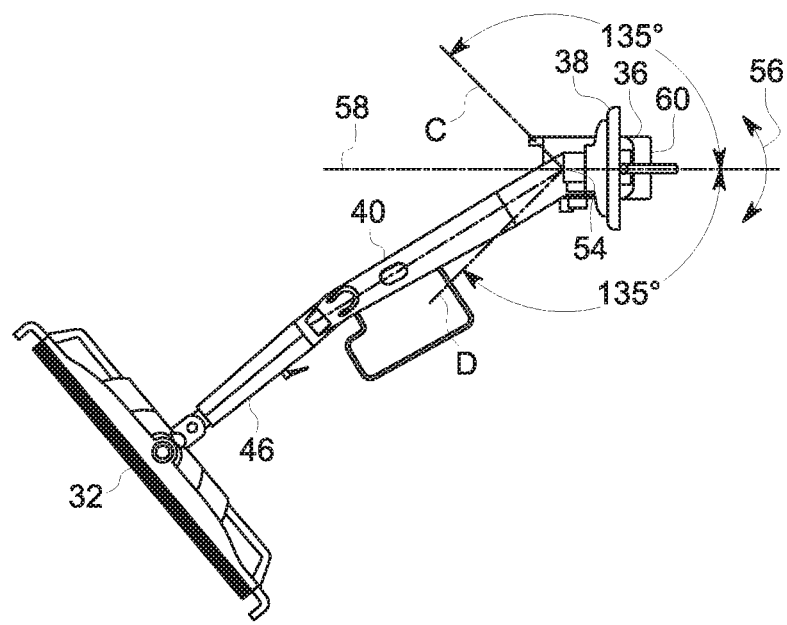
FIG. 3 is a top view of an embodiment of the extension arm having the first monitor and the support for the second monitor coupled to the portion (e.g., arm base) of the X-ray imaging system of FIG. 1 illustrating the rotational movement of the support.

As depicted in FIG. 3, rotation of the support 52 in the circumferential direction 56 about the coaxial axis 54 enables the second monitor 34 to be rotated up to approximately 270 degrees about the axis 54. In particular, the second monitor 34 may be rotated (e.g., on a side 60 of the base portion 36 facing away from the C-arm 14) approximately 135 degrees between the longitudinal axis 58 of the base portion 36 (or cross arm 22) and point C (located to the left of the axis 58 relative to the side 60). The second monitor 34 may also be rotated approximately 135 degrees (in the opposite direction) between the longitudinal axis 58 and point D (located to the right of the axis 58 relative to the side 60).

Figure 4:
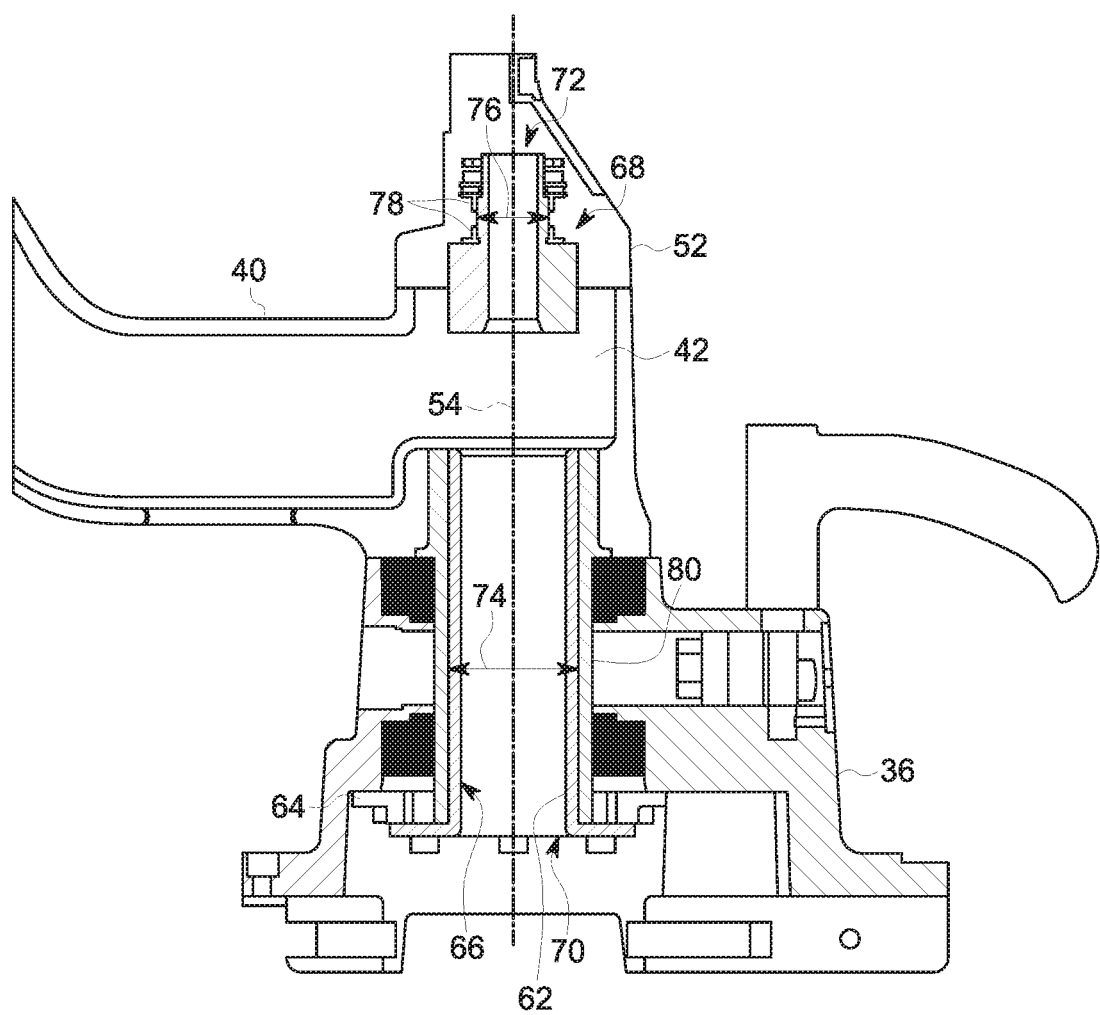
FIG. 4 is a partial cutaway cross-sectional view of an embodiment of a coupling mechanism of the support to the X-ray imaging system of FIG. 1.

FIG. 4 is a partial cutaway cross-sectional view of an embodiment of a coupling mechanism of the support 52 to the X-ray imaging system 10 of FIG. 1. In particular, FIG. 4 depicts how the support 52 is coupled to the base portion 36. As depicted, a pole or rod 62 is coupled to the base portion 36 via a plate 64 (e.g., connecting plate) fastened (e.g., bolted or screwed) to the base portion 36. The pole 62 may be made of metal (e.g., aluminum). The pole 62 extends vertically from the base portion 36 along the axis 54. A portion 66 of the pole 62 is disposed within the base portion 36, while a portion 68 extends out from the base portion 36. End 70 of the pole 62 is coupled to the plate 64, while end 72 of the pole 62 is coupled to the support 52. The portion 66 includes a diameter 74 that is greater than a diameter 76 of the portion 68 adjacent the end 72. A pair of bearings 78 (e.g., plastic bearings) are disposed about the portion 68 of the pole 62 adjacent the end 72. The pole 62 is stationary relative to the base portion 36, while the bearings 78 enable rotation of the support 52 (and the second monitor 34) about both the pole 62 and the axis 54.

Figure 5:
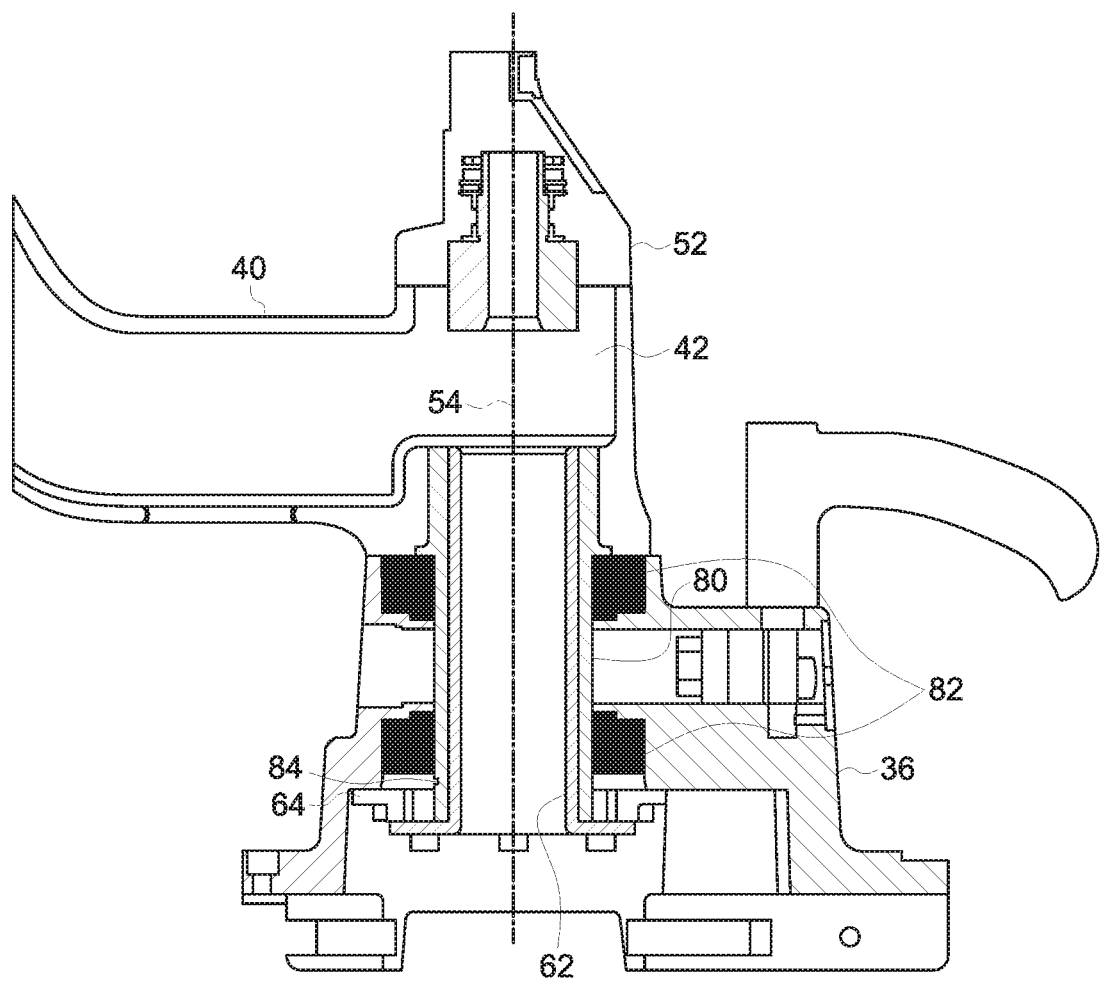
FIG. 5 is a partial cutaway cross-sectional view of an embodiment of a coupling mechanism of the extension arm to the X-ray imaging system of FIG. 1.

At least the portion 66 of the pole 62 is concentrically disposed within a tube 80 (see FIG. 5). The end 42 of the extension arm 40 is disposed about the tube 80 and the pole 62. Thus, the pole 62 extends through the end 42 of the extension arm 40. The support 52 is coupled to the pole 62 above the end 42 of the extension arm 40. As depicted, the end of the extension arm 40 and the support 52 are vertically aligned.

FIG. 5 is a partial cutaway cross-sectional view of an embodiment of a coupling mechanism of the extension arm 40 to the X-ray imaging system 10 of FIG. 1. In particular, FIG. 5 depicts how the extension arm 40 is coupled to the base portion 36. As mentioned above, the tube 80 is concentrically disposed about the pole 62. The pole 62 may be made of metal (e.g., steel). The end 42 of the extension arm 40 is coupled to the tube 80. Below the end 42 of the extension arm 40 (between the end 42 and the plate 64) a pair of bearings 82 are disposed about the tube 80. The bearings 82 enable rotation of the tube 80 (about the axis 54 and the pole 62) and, thus, rotation of the extension arm 40 (and the first monitor 32). A clip 84 disposed about and coupled to the tube 80 directly above the plate 64 maintains the vertical position of the tube 80. The bearings 82 are coupled to the base portion 36 via an interference fit. A clearance fit is provided between the bearings 82 and the tube 82. The tube 80 (integrated in the extension arm 40) may be manually disposed within a hole of the bearings 80. The coupling mechanism, as described in FIGS. 4 and 5, enables the independent rotation of the support 52 and extension arm 40 (and, thus, the monitors 32, 34) about the axis 54.

Technical effects of the disclosed embodiments include providing a compact C-arm imaging system that enables independent rotation of different monitors about a coaxial axis. In particular, an extension arm coupled to a first monitor may rotate independently about the coaxial axis without affecting a position of a second monitor, while a support coupled to a second monitor (e.g., as part of a computing device) may rotate independently about the coaxial axis without affecting a position of the first monitor. This enables medical personnel (e.g., doctor, technician, etc.) to perform their respective tasks without interference (e.g. due to unwanted movement of their respective monitor) on the compact mobile C-arm imaging system.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An X-ray imaging system, comprising:
   an X-ray radiation source;
   an X-ray detector;
   a C-arm having the X-ray radiation source disposed on a first end and the X-ray detector disposed on a second end opposite the first end;
   a base coupled to the C-arm;
   a first monitor coupled to the base;
   a second monitor coupled to the base, wherein the first monitor and the second monitor are configured to rotate independent of each other about a common rotational axis;
   an extension arm having a third end and a fourth end, wherein the first monitor is coupled to the third end of the extension arm, and the extension arm is configured to rotate the first monitor about the common rotational axis;
   a support, wherein the support is coupled both to the base and the second monitor, and the support is configured to rotate the second monitor about the common rotational axis; and
   a pole coupled to the base, and a tube concentrically disposed about a portion of the pole, wherein the support is coupled to the pole, and the extension arm is coupled to the tube.

2. The X-ray imaging system of claim 1, wherein the extension arm is configured to rotate the first monitor 210 degrees about the common rotational axis.

3. The X-ray imaging system of claim 1, comprising a spring arm having a fifth end and a sixth end, wherein the fifth end is coupled to the first monitor and the sixth end is coupled to the third end of the extension arm.

4. The X-ray imaging system of claim 1, wherein the fourth end of the extension arm is coupled to the base.

5. The X-ray imaging system of claim 1, wherein the support is configured to rotate the second monitor 270 degrees about the common rotational axis.

6. The X-ray imaging system of claim 1, comprising a computing device, wherein the computing device comprises the second monitor and is configured to control operation of the X-ray imaging system.

7. A C-arm X-ray imaging system, comprising:
   a base;
   an extension arm;
   a first monitor coupled to the base via a first end of the extension arm;
   a support;
   a second monitor coupled to the base via the support, wherein the first end of the extension arm and the support are vertically aligned and configured to rotate about a common rotational axis to enable independent rotation of the first and second monitors; and a pole coupled to the base, and a tube concentrically disposed about a portion of the pole, wherein the support is coupled to the pole, and the first end of the extension arm is coupled to the tube.

8. The C-arm X-ray imaging system of claim 7, wherein the pole extends through the first end of the extension arm.

9. The C-arm X-ray imaging system of claim 8, wherein the pole is stationary relative to the base, and the first end of the extension arm and the tube are configured to rotate about the pole.

10. The C-arm X-ray imaging system of claim 9, comprising a first pair of bearings disposed about both the pole and the tube and a second pair of bearings disposed about the pole, wherein the first pair of bearings is configured to enable the extension arm to rotate about the common rotational axis, and the second pair of bearings is configured to enable the support to rotate about the common rotational axis.

11. The C-arm X-ray imaging system of claim 10, comprising a clip disposed about the tube and to maintain a vertical position of the first pair of bearings relative to the tube.

12. The C-arm X-ray imaging system of claim 7, wherein the extension arm is configured to rotate the first monitor 210 degrees about the common rotational axis, and the support is configured to rotate the second monitor 270 degrees about the common rotational axis.

13. A C-arm X-ray imaging system, comprising:
a base;
an extension arm;
a first monitor coupled to the base via an end of the extension arm;
a support;
a computing device coupled to the base via the support, wherein the computing device comprises a second monitor and the computing device is configured to control operation of the C-arm X-ray imaging system, and wherein the first monitor and the second monitor are configured to rotate independent of each other about a coaxial axis; and
a pole coupled to the base, and a tube concentrically disposed about a portion of the pole, wherein the support is coupled to the pole, the end of the extension arm is coupled to the tube, and the end of the extension arm and the support are vertically aligned about the coaxial axis.

14. The C-arm X-ray imaging system of claim 13, wherein the first monitor is configured to rotate 210 degrees about the coaxial axis.

15. The C-arm X-ray imaging system of claim 14, wherein the second monitor is configured to rotate 270 degrees about the coaxial axis.

* * * * *